United States Patent [19]
Ham et al.

[11] Patent Number: 5,456,667
[45] Date of Patent: Oct. 10, 1995

[54] TEMPORARY STENTING CATHETER WITH ONE-PIECE EXPANDABLE SEGMENT

[75] Inventors: Kevin Ham, Santa Clara; Michi E. Garrison; Farhad Khosravi, both of Belmont, all of Calif.

[73] Assignee: Advanced Cardiovascular Systems, Inc., Santa Clara, Calif.

[21] Appl. No.: 64,966

[22] Filed: May 20, 1993

[51] Int. Cl.⁶ .................................................. A61M 29/00
[52] U.S. Cl. .......................... 604/107; 604/104; 606/194; 606/198
[58] Field of Search ...................... 604/93, 102, 104–109, 604/280, 282, 96, 49–53, 171, 175; 606/108, 191, 192, 194, 198; 623/1, 11, 12

[56] References Cited

U.S. PATENT DOCUMENTS

| | | |
|---|---|---|
| 3,105,492 | 10/1963 | Jeckel . |
| 3,713,175 | 1/1973 | Weisman . |
| 3,868,956 | 3/1975 | Alfidi et al. . |
| 4,130,904 | 12/1978 | Whalen . |
| 4,300,244 | 11/1981 | Bokros . |
| 4,315,513 | 2/1982 | Nawash .................................. 604/175 |
| 4,503,569 | 3/1985 | Dotter . |
| 4,512,338 | 4/1985 | Balko et al. . |
| 4,534,349 | 8/1985 | Barrows . |
| 4,553,545 | 11/1985 | Maass et al. . |
| 4,585,000 | 4/1986 | Hershenson . |
| 4,619,246 | 10/1986 | Molgaard-Nielsen et al. . |
| 4,649,922 | 3/1987 | Wiktor . |
| 4,650,466 | 3/1987 | Luther . |
| 4,655,771 | 4/1987 | Wallsten . |
| 4,662,885 | 5/1987 | DiPisa, Jr. . |
| 4,681,110 | 7/1987 | Wiktor . |
| 4,699,611 | 10/1987 | Bowden .................................. 604/51 |
| 4,705,517 | 11/1987 | DiPisa, Jr. . |
| 4,706,671 | 11/1987 | Weinrib . |
| 4,718,907 | 1/1988 | Karwoski et al. . |
| 4,733,665 | 3/1988 | Palmaz . |
| 4,739,762 | 4/1988 | Palmaz . |
| 4,740,207 | 4/1988 | Kreamer . |
| 4,762,128 | 8/1988 | Rosenbluth . |
| 4,768,507 | 9/1988 | Fischell et al. . |
| 4,776,337 | 10/1988 | Palmaz . |
| 4,800,882 | 1/1989 | Gianturco . |
| 4,830,003 | 5/1989 | Wolff et al. . |
| 4,856,516 | 8/1989 | Hillstead . |
| 4,877,030 | 10/1989 | Beck et al. . |
| 4,878,906 | 11/1989 | Lindemann et al. . |
| 4,886,062 | 12/1989 | Wiktor . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,950,227 | 8/1990 | Savin et al. . |
| 4,969,458 | 11/1990 | Wiktor . |
| 4,969,890 | 11/1990 | Sugita et al. . |
| 4,969,891 | 11/1990 | Gewertz . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold et al. . |
| 5,007,926 | 4/1991 | Derbyshire . |
| 5,015,253 | 5/1991 | MacGregor . |

(List continued on next page.)

FOREIGN PATENT DOCUMENTS

| 8215358 | 9/1992 | WIPO ..................................... 604/105 |
|---|---|---|

Primary Examiner—C. Fred Rosenbaum
Assistant Examiner—Chalin Smith
Attorney, Agent, or Firm—Fulwider Patton Lee & Utecht

[57] ABSTRACT

An intravascular catheter with an expandable region formed of a tubular material that continues the distal end of the catheter body in a one-piece configuration and is radially expanded and contracted by means of a control wire. The interior of the expandable region is in fluid communication with a lumen in the catheter body to allow the delivery of a fluid to the artery via openings in the surface of the expandable region. The catheter is particularly adapted to hold open an artery after a vascular procedure therein such as a balloon or other type of angioplasty, and if desired to introduce a therapeutic drug or other fluid to the site of the vascular procedure.

14 Claims, 3 Drawing Sheets

U.S. PATENT DOCUMENTS

| | | | |
|---|---|---|---|
| 5,019,085 | 5/1991 | Hillstead . | |
| 5,019,090 | 5/1991 | Pinchuk . | |
| 5,026,377 | 6/1991 | Burton | 606/108 |
| 5,034,001 | 7/1991 | Garrison | 606/53 |
| 5,035,706 | 7/1991 | Giantureo et al. . | |
| 5,037,392 | 8/1991 | Hillstead . | |
| 5,037,427 | 8/1991 | Harada et al. . | |
| 5,041,093 | 8/1991 | Chu | 604/104 |
| 5,041,126 | 8/1991 | Gianturco . | |
| 5,059,211 | 10/1991 | Stack et al. . | |
| 5,061,275 | 10/1991 | Wallsten et al. . | |
| 5,064,435 | 11/1991 | Porter . | |
| 5,071,407 | 12/1991 | Termin | 604/104 |
| 5,078,726 | 1/1992 | Kreamer . | |
| 5,078,736 | 1/1992 | Behl . | |
| 5,084,065 | 1/1992 | Weldon et al. . | |
| 5,089,005 | 1/1992 | Harada . | |
| 5,089,006 | 2/1992 | Stiles . | |
| 5,092,877 | 3/1992 | Pinchuk . | |
| 5,100,429 | 3/1992 | Sinofsky et al. . | |
| 5,102,417 | 4/1992 | Palmaz . | |
| 5,104,404 | 4/1992 | Wolff . | |
| 5,108,416 | 4/1992 | Ryan | 606/194 |
| 5,116,318 | 5/1992 | Hillstead . | |
| 5,116,360 | 5/1992 | Pinchuk et al. . | |
| 5,116,365 | 5/1992 | Hillstead . | |
| 5,122,154 | 6/1992 | Rhodes . | |
| 5,123,917 | 6/1992 | Lee . | |
| 5,133,732 | 7/1992 | Wiktor . | |
| 5,135,536 | 8/1992 | Hillstead . | |
| 5,147,370 | 9/1992 | McNamara | 606/194 |
| 5,147,385 | 9/1992 | Beck et al. . | |
| 5,156,620 | 10/1992 | Pigott . | |
| 5,161,547 | 11/1992 | Tower . | |
| 5,163,951 | 11/1992 | Pinchuk et al. . | |
| 5,163,952 | 11/1992 | Froix . | |
| 5,163,958 | 11/1992 | Pinchuk . | |
| 5,171,262 | 12/1992 | MacGregor . | |
| 5,190,058 | 3/1993 | Jones et al. . | |
| 5,192,297 | 3/1993 | Hull . | |
| 5,192,307 | 3/1993 | Wall . | |
| 5,192,311 | 3/1993 | King et al. . | |
| 5,193,533 | 3/1993 | Body | 604/105 |
| 5,195,984 | 3/1993 | Schatz . | |
| 5,197,978 | 3/1993 | Hess . | |
| 5,222,971 | 6/1993 | Willard et al. | 606/158 |
| 5,226,913 | 7/1993 | Pinchuck . | |
| 5,232,440 | 8/1993 | Wilk | 604/49 |

TEMPORARY STENTING CATHETER WITH ONE-PIECE EXPANDABLE SEGMENT

BACKGROUND OF THE INVENTION

This invention generally relates to vascular catheters suitable for maintaining the patency of a blood vessel after a vascular procedure therein, such as angioplasty.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guidewire and a dilatation catheter having an inflatable balloon on the distal end thereof are introduced through the guiding catheter with the guidewire slidably disposed within an inner lumen of the dilatation catheter. The guidewire is first advanced out of the distal end of the guiding catheter and is then maneuvered into the patient's coronary vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., greater than about 4 atmospheres) and is inflated to a predetermined size (preferably the same as the inner diameter of the artery at that location) to radially compress the atherosclerotic plaque of the lesion against the inside of the artery wall to thereby dilate the lumen of the artery. The balloon is then deflated so that the dilatation catheter can be removed and blood flow resumed through the dilated artery.

By way of example, further details of angioplasty procedures and the devices used in such procedures can be found in U.S. Pat. No. 4,323,071 (Simpson-Robert), U.S. Pat. No. 4,332,254 (Lindquist), U.S. Pat. No. 4,439,185 (Lundquist), U.S. Pat. No. 4,168,224 (Enzmann, et al.), U.S. Pat. No. 4,516,972 (Samson), U.S. Pat. No. 4,582,181 (Samson), U.S. Pat. No. 4,538,622 (Samson, et al.), U.S. Pat. No. 4,597,755 (Samson), U.S. Pat. No. 4,616,652 (Simpson), U.S. Pat. No. 4,748,982 (Horzewski, et al.), U.S. Pat. No. 4,771,778 (Mar), and U.S. Pat. No. 4,793,350 (Mar, et al.) which are hereby incorporated herein in their entirety.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon the deflation of the balloon, a section of the dissected lining (commonly termed a "flap") will collapse into the bloodstream, thereby closing or significantly reducing the blood flow through the vessel. In these instances, emergency bypass surgery is usually required to avoid a myocardial infarct distal to the blockage.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In recent years, various devices and methods (other than bypass surgery) for prevention of restenosis and repairing damaged blood vessels have become known which typically use an expandable cage or region (commonly termed "stent") on the distal end of the catheter designed to hold a detached lining against an arterial wall for extended periods to facilitate the reattachment thereof. Some stents are designed for permanent implantation inside the blood vessel and others are designed for temporary use in the vessel. By way of example, several stent devices and methods can be found in U.S. Pat. No. 4,998,539, U.S. Pat. No. 5,002,560, U.S. Pat. No. 5,034,001 (Garrison, et al.), U.S. Pat. No. 5,133,732 (Wiktor), and U.S. Pat. No. 5,180,368 (Garrison).

Typically, the expandable region of these stents is formed by a braided wire attached to the distal end of the catheter body. Such braided designs are difficult and expensive to manufacture, and create reliability concerns due to the existence of high stress points located at the connection of the braided wire region with the catheter body and at the connections between the intermingled wire strands.

What has been needed and heretofore unavailable is an easily advanceable and removable low-profile intravascular catheter which can hold a collapsed dissected lining or flap against the blood vessel wall for sufficient time to allow the natural adhesion of the flap to the blood vessel wall by utilizing a stent design that continues the tubular catheter body in a one-piece configuration which eliminates the need for joining the material forming the stent (expandable region) to the material forming the catheter body. Such a stent would have to be easy and inexpensive to manufacture, strong and reliable under pressure, and capable of being formed in a variety of shapes to allow flexibility in the amount and pattern of expansion and deformation of the expandable region and other parameters that are related to the use and function of the device. The present invention fulfills this need.

SUMMARY OF THE INVENTION

This invention is directed to a vascular catheter with an expandable region continuing the catheter body in a one-piece configuration which can hold a blood vessel open for a long period of time after a vascular procedure therein in order to allow the interior of the vessel to be repaired while the flow of blood continues through the vessel. In addition to using the vascular catheter of the invention to repair injury to a blood vessel caused after a balloon angioplasty, the invention may also be used as an emergency device to allow repair of damage to a blood vessel after medical therapies such as atherectomy, implanting stents, or surgical bypass, where a vessel wall is in danger of collapsing, tearing, or restricting blood flow.

The vascular catheter in accordance with the present invention includes an elongated catheter body formed by a tubular member having a first inner lumen which extends through essentially the entire length of the body and a second, much shorter lumen in the distal portion of the catheter body which is adapted to receive a guiding member therein and which extends through the distal portion from a proximal opening in the sidewall of the distal portion to an opening in the distal end of the catheter body.

An expandable region formed of the same material that forms the catheter body continues the catheter body in a one-piece configuration. The proximal end of the expandable region begins at the distal end of the catheter body and the distal end of the expandable region is provided with an opening which allows for the passage of a guiding member therethrough. Since the expandable region is a continuation of the tubular member forming the catheter body, the proximal end of the expandable region is fixed in place, but the distal end of the expandable region is free to move longitudinally relative to the catheter body.

It must be noted that although the advantages of the present invention are realized by the one-piece configuration of the expandable region as a continuation of the catheter body, it is also possible (although not advantageous) to form a similarly-shaped expandable region as in the invention, of a separate piece of material attached to the catheter body. This separate form of the expandable region is not described herein.

The one-piece expandable region is formed by etching, machining or otherwise removing portions of the same tubular material that forms the catheter body. Therefore, the length of the tubing material selected must be substantially equal to the combined lengths of the catheter body and the expandable region. Removal of portions of the tubular material forming the expandable region creates a pattern therein, so that when the distal end of the expandable region is moved proximally in the direction of the catheter body, the tubular material forming the expandable region may deform into a sufficiently smooth-shaped structure with a larger diameter than the tubular catheter body.

A control wire extends through the first inner lumen of the tubular member and the interior of the expandable region with the distal end thereof connected to the distal collar which is secured to the distal end of the expandable region. A flexible tubular guide, such as a coiled spring or a flexible tubular member, is provided on the interior of the expandable region between the ends thereof to ensure the proper passage of the guidewire therethrough. If not properly guided, the guidewire can diverge out of its travel path and move towards the inside of the expandable region. Longitudinal movement of the control wire forces the distal collar and the distal end of the expandable region that is connected to the distal collar to move accordingly. Such movement adjusts the axial spacing between the proximal and distal ends of the expandable region which thereby allows the tubular material forming the expandable region to deform to a larger diameter when the control wire is moved proximally and extend to its original diameter when the control wire is extended distally. Preferably, the control wire is sufficiently stiff so that movement thereof in the distal direction will cause the expandable region to elongate without bending or kinking the wire. This eliminates the need for biasing the expandable region in some manner to return to an elongated state with minimal radial dimensions after the expansion thereof to allow for the ready removal of the catheter from the blood vessel. A suitable manipulator is provided on the proximal end of the catheter assembly to longitudinally move the control wire within the first lumen of the tubular member.

The relatively short, second inner lumen disposed within the distal portion of the tubular member is preferably defined in part by a sidewall in the distal portion of the tubular member which is provided with an elongated slot extending distally from the proximal hole in the sidewall to a location proximally adjacent the proximal end of the expandable region. This slotted construction greatly facilitates the rapid exchange of the vascular device of the invention over an in-place guidewire.

The proximal opening or port of the second inner lumen should be spaced proximally more than about 15 cm but less than about 60 cm, preferably from about 20 cm to about 50 cm, from the distal end of the catheter to ensure that the proximal opening in the sidewall of the tubular body does not extend beyond the distal end of the guiding catheter during a vascular procedure because the guidewire tends to form a loop if not restrained in some manner when the vascular catheter of the invention is pulled proximally. Loop formation can interfere with the subsequent removal of the catheter device through the guiding catheter.

In a presently preferred embodiment, the proximal portion of the tubular body is provided with a third inner lumen which has disposed therein a stiffening member or stylet which adds to the pushability of the catheter and facilitates the advancement thereof through a patient's vascular system.

The vascular catheter of the invention allows for the rapid advancement thereof over a guidewire or other guiding member to a vascular location wherein an occlusion has occurred. The expandable region when expanded will hold the blood vessel open and simultaneously allow blood flow through the expandable region thereby eliminating or preventing ischemic conditions distal to the occlusion. Importantly, the expandable region of the vascular catheter of the present invention continues the catheter body in a one-piece configuration, thus eliminating joints and improving reliability of the expandable region during expansion. In addition, formation of the expandable region by removing portions of a tubular body provides design flexibility so that the expandable region can be formed by removing varying portions of the tubular material to respond to specific requirements related to the use and function of the device such as the amount and pattern of expansion and deformation, and axial flexibility of the expandable region. Also, the vascular catheter of the invention can be mounted and withdrawn from an in-place guidewire without the use of extension wires and the like which can greatly increase the overall time for the procedure. These and other advantages of the invention will become more apparent from the following detailed description thereof when taken in conjunction with the accompanying exemplary drawings.

DETAILED DESCRIPTION OF THE INVENTION

FIGS. 1–4 illustrate an intravascular catheter assembly 10 embodying features of the invention. Catheter assembly 10 generally includes an elongated catheter body 11, an expandable region 12 beginning at the distal end of the catheter body and continuing the catheter body in a one-piece configuration, and a control wire or cable 13 for adjustment of the axial distance between proximal end 14 and distal end 15 of expandable region 12 to vary the radial expansion thereof.

The elongated tubular member which forms catheter body 11 has a first inner lumen 17 which extends through essentially the entire length thereof and which is adapted to receive control wire 13 and a second much shorter inner lumen 20 in the distal portion of catheter body 11 which extends from side port 21 in sidewall 22 of tubular catheter body 11 to port 23 provided in the distal end of the catheter body. A guiding member 24 is slidably disposed within the relatively short inner lumen 20 to facilitate the rapid advancement and replacement of catheter assembly 10. A longitudinal slit 25 is preferably provided in sidewall 22 which extends distally from side port 21. A third inner lumen 26 may be provided within catheter body 11 which extends from a location proximal to side port 21 to essentially the proximal end of the tubular member. A rod or stylet 27 fits within third inner lumen 26 to provide additional stiffness to catheter assembly 10 proximal to side port 21 to increase its pushability.

Expandable region 12 is formed by removing portions of the tubular material forming elongated catheter body 11 by etching, machining, or otherwise creating a pattern in the tubular material to allow it to deform into a larger diameter than the diameter of the tubular catheter body. The patterns for the formation of the expandable region can vary considerably as the choice of the pattern can affect the amount of material deformation, the amount of shortening of the expandable region during expansion, the radial forces exerted by and upon the expandable region, the diameter of the expanded region, the axial flexibility of the expandable region, and other parameters related to the performance of the expandable region. In a presently preferred embodiment, shown in FIG. 1, a spiral pattern is created in the tubular body forming expandable region 12. By way of example, two other alternatives of many possible patterns for the formation of the expandable region are shown in FIGS. 5, 5a, 6, and 6a. A flexible tubular element 29 is provided within the interior of expandable region 12 between proximal and distal ends 14 and 15 thereof to guide guiding member 24 through the interior of the expandable region. Distal end 15 of expandable region 12 is bonded by suitable means such as an adhesive to distal collar 31 which has a central passageway for the guiding member to be advanced therethrough. The distal end of control wire 13 is also fixed to distal collar 31 which is slidably mounted about flexible tubular element 29 so that longitudinal or axial movement thereof adjusts the axial spacing between proximal and distal ends 14 and 15 of the expandable region, thereby varying the radial dimension thereof. The material remaining in the tubular body forming expandable region 12 should have sufficient strength so that the expandable region is capable of supporting an external pressure of at least 4 psi to ensure that a flap can be properly held in position within a patient's artery.

Figure 1:
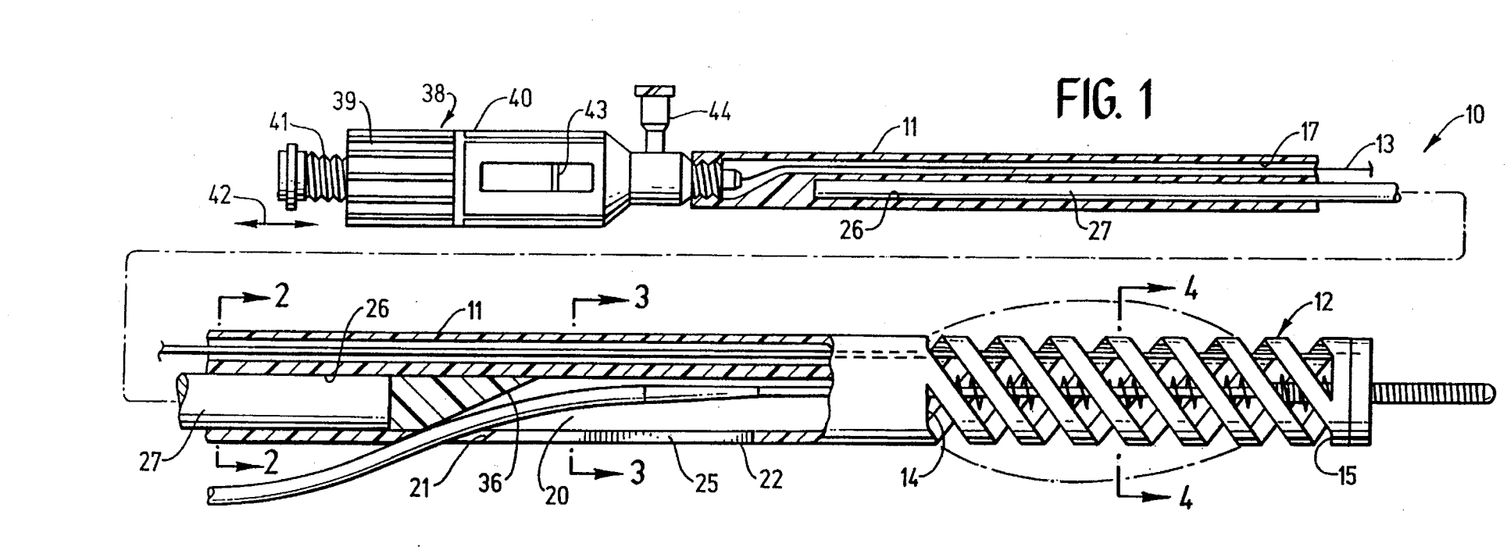
FIG. 1 is an elevational view, partially in cross-section, of an intravascular catheter embodying features of the invention.
Figure 1A:
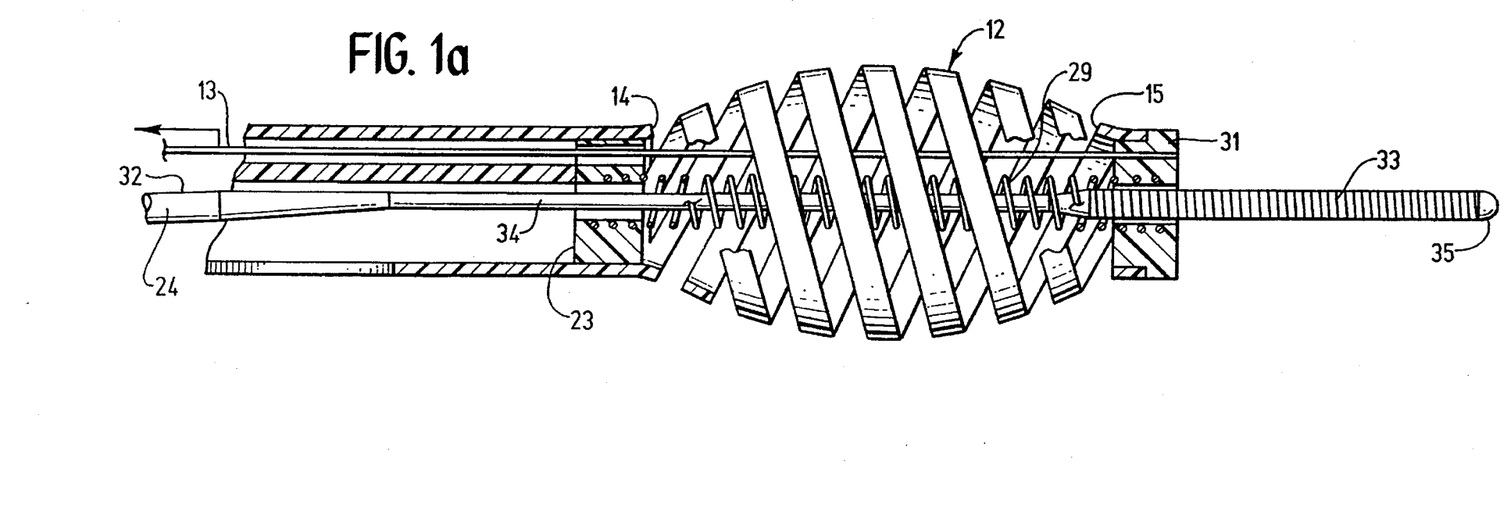
FIG. 1a is an elevational view of the expandable region of the catheter shown in FIG. 1 in the expanded condition.
Figure 2:
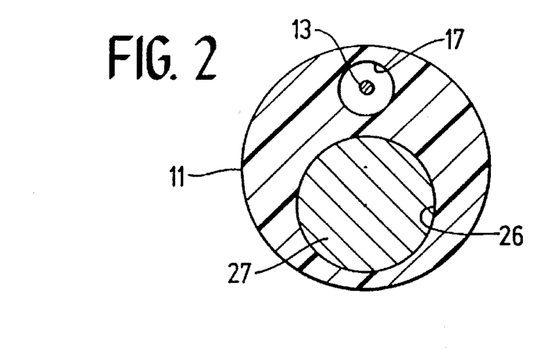
FIG. 2 is a transverse cross-sectional view of the catheter shown in FIG. 1 taken along lines 2—2.
Figure 3:
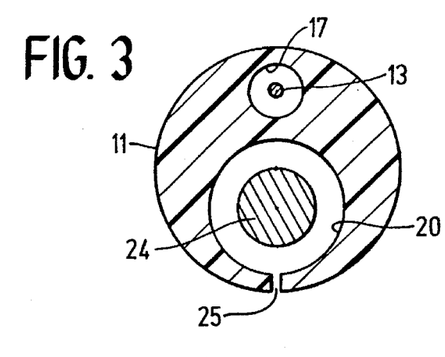
FIG. 3 is a transverse cross-sectional view of the catheter shown in FIG. 1 taken along lines 3—3.
Figure 4:
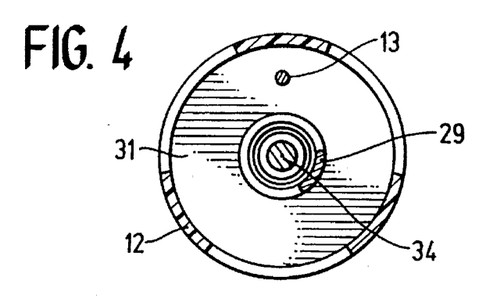
FIG. 4 is a transverse cross-sectional view of the catheter shown in FIG. 1 taken along lines 4—4.

Guidewire 24 comprises a core member 32, a helical coil 33 or other flexible body disposed about and fixed to the tapered distal portion 34 of the core member. A rounded plug 35, preferably formed of radiopaque material, is provided at the distal tip of coil 33. The construction of the distal portion of guidewire 24 can have a conventional structure with core member 32 extending through helical coil 33 to plug 35 or with the core member terminating short of plug 35 and a shaping ribbon (not shown) extending from core member 32 to plug 35. Guide member 24 extends through second inner lumen 20 disposed within the distal portion of tubular member and out distal port 23, through the flexible tubular guiding element 29 which extends through the interior of expandable region 12 and out the distal end thereof through distal collar 31. An incline or ramp 36 is provided at the proximal end of second inner lumen 20 at the entryway of side port 21 to facilitate the insertion and withdrawal of guidewire 24 therethrough.

The distance between distal end 15 of expandable region 12 and side port 21 should be at least 15 cm but not greater than 60 cm, preferably from about 20 to about 50 cm, so that when the expandable region is expanded within a patient's vascular system to hold a blood vessel open, side port 21 of catheter assembly 10 will remain within the interior of a guiding catheter to ensure that guiding member 24 does not have the opportunity to form a loop when the catheter assembly is pulled back into the guiding catheter.

A manipulator adapter 38 is provided on the proximal end of catheter body 11 to effect longitudinal movement of control wire 13. Internally threaded cap 39 is secured to the proximal end of manipulator housing 40. Axial rotation of cap 39 causes the longitudinal movement of internal member 41 as shown by arrow 42, and as a result controls the axial spacing between proximal and distal ends 14 and 15 of expandable region 12 and thus the radial dimension thereof. If control wire 13 is relatively stiff, it can be employed to extend ends 14 and 15 of expandable region 12 away from one another, elongating the expandable region so that it can be removed from a blockage. If not, control wire 13 can be used to shorten the spacing between ends 14 and 15, but the expandable region can be formed in a biased condition so that upon release of the manipulator, the expandable region returns to its elongated condition. An indicator 43 is provided on internal member 41 to display the radial dimension of expandable region 12.

Other means can be employed to expand expandable region 12 and return it to an elongated condition. For example, as previously mentioned a spring may be provided between ends 14 and 15 and be biased to cause the same elongation. Additionally, the tubular material of the expandable region can be formed of a material such as a nickel-titanium alloy (commonly referred to as "nitinol") which has a shape-memory property to allow expandable region 12 to change shape with changes in temperature. An electrical current can be passed through the material forming the expandable region to resistively heat the material and thereby change the shape thereof or a hot or cold fluid could be introduced to trigger a mechanical response resulting in a change in the shape. The expandable region could also be formed with a memory to either expand or contract in response to a temperature variance. In such a case, the control wire could be used to return the expandable region to the desired shape. It is also possible to set the shape memory temperature of the expandable region well below that of the blood to give the expandable region pseudoelastic properties. In such a case, pulling control wire 13 will cause expandable region 12 to expand and releasing the control wire will cause the expandable region to collapse or extend to its original position. When the expandable region is formed of a material that would take its expanded shape when unconstrained, it is possible to use an outer sleeve (not shown) around the expandable region to constrain the expandable region to its elongated shape during the placement of the catheter assembly in the patient's artery followed by the removal of the sleeve when expansion of the expandable region is desired, and reusing the sleeve before removal of the expandable region and the catheter assembly from the artery.

Manipulator 38 has a side arm 44 to inject therapeutic drugs or other desired fluids such as heparinized saline through first inner lumen 17. Solutions such as heparinized saline can be used to keep the lumen free of blood and to prevent the formation of thrombi in the inner lumen or in expandable region 12. Further details of the manipulator 38 can be found in U.S. Pat. No. 5,002,560 entitled EXPANDABLE CAGE CATHETER WITH A ROTATABLE GUIDE.

Generally, the dimensions of the catheter assembly of the invention are essentially the same dimensions of vascular catheters used in angioplasty procedures. The overall length of the assembly may be about 100 to 175 cm. The diameter of the catheter body may range from about 0.035 to 0.06 inch. The expandable region in the unexpanded condition has approximately the same diameter as the catheter body but may be expanded to a maximum diameter of about 1 to about 10 mm. The diameter of first inner lumen 17 will depend upon the size of control wire 13 and the amount of fluid or drugs which will be passed therethrough. The diameter of second inner lumen 20 should be sufficiently larger than the diameter of guiding member 24 to allow the catheter to be easily advanced and removed over the guiding member.

In the operation of catheter assembly 10, the distal end thereof is mounted onto the proximal end of a guiding member 24 such as a guidewire which has been positioned across the occluded portion of the arterial passageway. The proximal end of the guiding member is advanced proximally through the central passageway provided in distal collar 31, guided through the interior of expandable region 12 by flexible tubular guiding element 29 through port 23 leading into second inner lumen 20, through the second inner lumen, and then out side port 21. The proximal portion of guiding member 24 extending out of side port 21 is then manually held while catheter assembly 10 is advanced over the guiding member through a previously positioned guiding catheter to a desired location within the patient's blood vessel, such as where a prior vascular procedure has been performed. Cap 39 on manipulator 38 is rotated to expand expandable region 12 and thereby to press a flap which may be obstructing the blood flow against the arterial wall and thereby maintain the patency of the artery. Expandable region 12 is held in the expanded condition for sufficient time, typically about 15 minutes to 24 hours, to allow the dissected lining to heal with the flap being reattached to the artery wall. Treatment periods of up to three days or more are believed to be beneficial. During the period of expansion of the expandable region, blood flows readily through the openings in the expandable region created by the removal of portions of the tubular material forming the expandable region so that no ischemia occurs distal to the catheter either in the occluded artery or a side branch thereof.

After the detached flap has been resecured to the artery wall, expanded region 12 can be elongated by rotating the cap in a direction opposite to the direction for expanding the expandable region to reduce the radial dimensions thereof. Then catheter assembly 10 can be removed from the location within the patient's vasculature.

As the distal section of the catheter body emerges from the proximal end of the guiding catheter, guiding member 24 can be separated from the second inner lumen by pulling the guidewire through slit 25 which extends from side port 21 to a location adjacent the proximal end of 14 of expandable region 12. This allows the guiding member to be manually held exterior to the guiding catheter while catheter assembly 10 of the invention is being exchanged for another catheter device.

Figure 5:
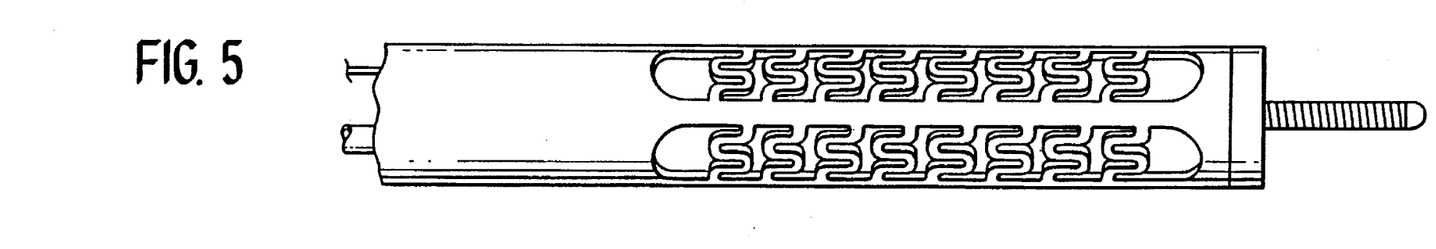
FIG. 5 is an elevational view of a first alternative embodiment of the expandable region of the catheter shown in FIG. 1, in the elongated condition.
Figure 5A:
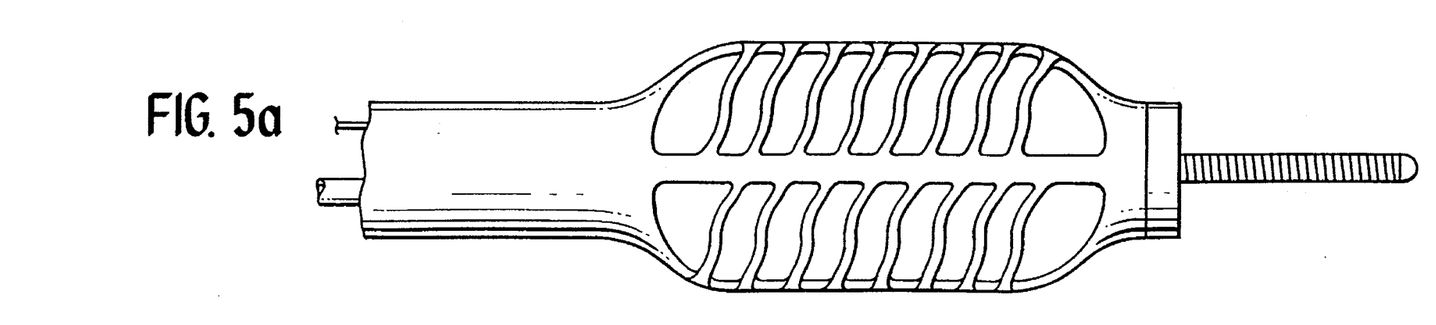
FIG. 5a is an elevational view of the expandable region shown in FIG. 5, in the expanded condition.
Figure 6:
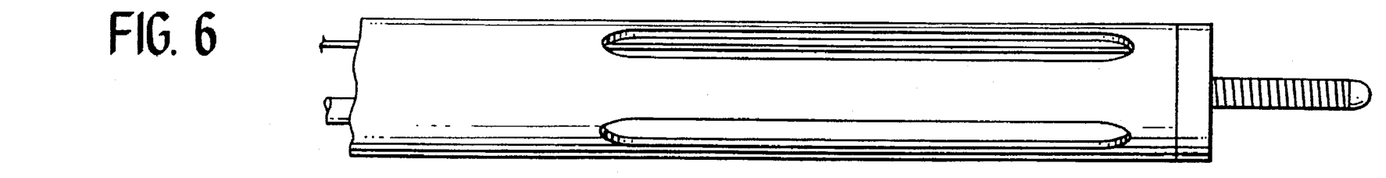
FIG. 6 is an elevational view of a second alternative embodiment of the expandable region of the catheter shown in FIG. 1, in the elongated condition.
Figure 6A:
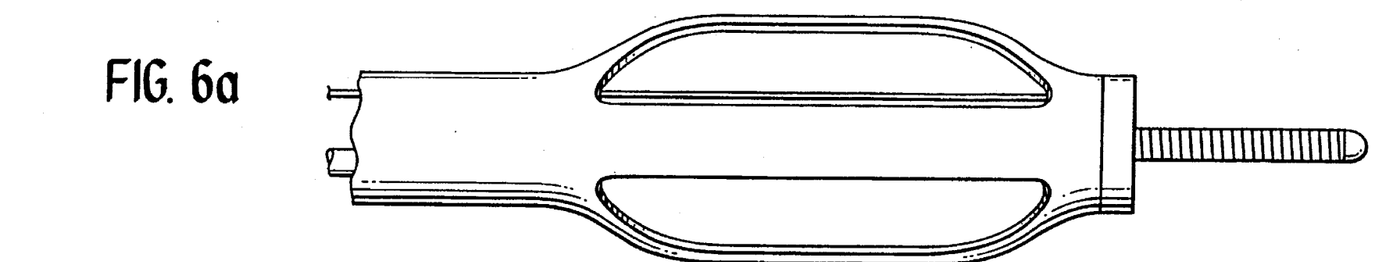
FIG. 6a is an elevational view of the expandable region shown in FIG. 6, in the expanded condition.

FIGS. 5 and 6 illustrate two alternative patterns for expandable region 12 in the extended position, while FIGS. 5a and 6a show these alternative patterns with the expandable region in the expanded position.

Figure 7:
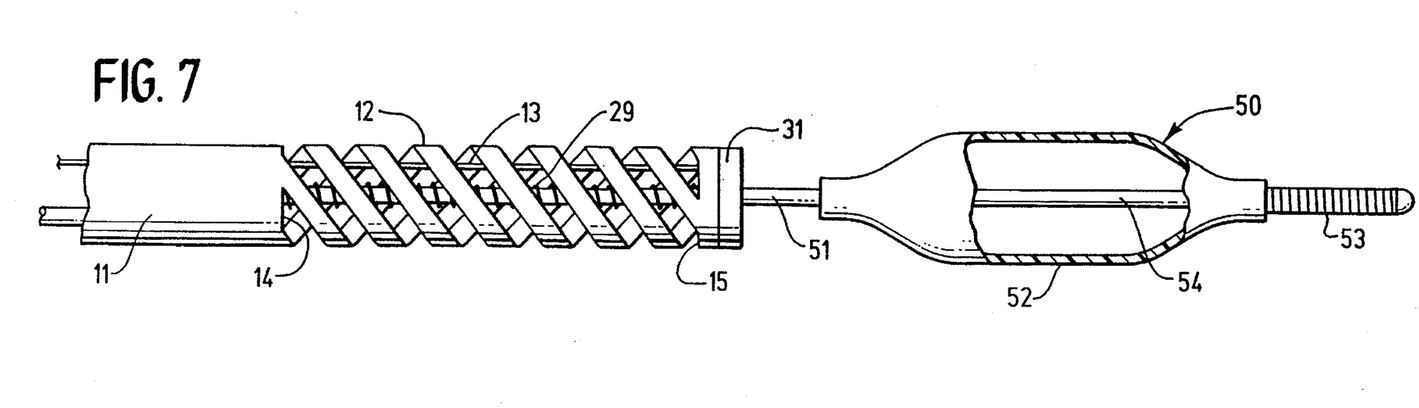
FIG. 7 is an elevational view of the intravascular device shown in FIG. 1, wherein the guiding member is a steerable low-profile dilatation catheter.

FIG. 7 illustrates an embodiment of the invention wherein guiding member 24 is a steerable low-profile dilatation catheter 50 which includes a tubular member 51, a dilatation balloon 52 and a helical coil 53 which is disposed about and secured to a core member 54. The proximal end of core member 54 may be secured to the interior of the distal portion of tubular member 51 or it may extend to the proximal end thereof. Further details of steerable dilatation catheters which are suitable for use as guiding members herein can be found in U.S. Pat. No. 4,582,350 (Samson), U.S. Pat. No. 4,771,778 (Mar), and U.S. Pat. No. 4,793,350 (Mar et al.), which have been previously incorporated herein, and U.S. Pat. No. 4,998,923 which is hereby incorporated herein in its entirety by reference. The operation and construction of these steerable dilatation catheters are adequately described in the aforesaid references and need not be repeated herein.

The catheter assembly of the invention is described herein to be employed after an angioplasty procedure to hold open an artery when a dissected portion of the arterial lining collapses and occludes the arterial lumen. Furthermore, the expandable region of the catheter of the invention may allow it to be used as a dilatation catheter. The assembly shown in FIG. 1 is particularly suitable for use with angioplasty catheters (not shown) having removable guiding members 24 such as disclosed in U.S. Pat. No. 4,323,071, previously referred to. The embodiment shown in FIG. 7 on the other hand includes a guiding member which is a low-profile steerable dilatation catheter. It will be recognized by those skilled in the art that the catheter of the invention can be used within a patient's vasculature system after vascular procedures other than angioplasty.

The catheter assembly of the invention may be formed of conventional materials of construction. The tubular material forming the catheter body and the expandable region can be made of any metal or polymer with ductile properties which would be acceptable for the specific needs of intravascular devices. Specifically, the material chosen for the catheter body and the expandable region would preferably provide sufficient hoop strength for the expandable region to serve as a temporary stent while having enough flexibility to advance the catheter assembly through tortuous anatomy. In addition, the portion of the material used to form the expandable region would preferably be sufficiently thin to allow the expandable region to expand easily. For example, catheter body 11 and the expandable region can be made of thin stainless steel tubing, nickel titanium alloy, polymer tubing and the like. A presently preferred material for the catheter body and the expandable region is stainless steel. Control wire 13 may be formed of stainless steel but may be formed of other materials such as platinum-nickel alloys (e.g., 90 wt % Pt, 10 wt % Ni) or suitable plastics or even composites. Variations can be made in the composition of the materials to vary properties.

As can be appreciated, various modifications can be made to the present invention. For example, the catheter assembly of the invention may be provided with an inflatable dilatation balloon proximal or distal to the expandable region. In this manner, after dilatation of a stenosis by such a balloon, the position of the catheter assembly can be quickly shifted to position the expandable region thereof within the occlusion so that the expandable region can be expanded to hold open the arterial passageway for sufficient time to tack up the flap against the arterial wall. Other modifications can be made to the present invention without departing from the scope thereof.

What is claimed is:

1. An intravascular catheter for maintaining the patency of an arterial vasculature for an extended period, the catheter comprising:

a) a catheter body having a proximal end and a distal end, said catheter body also having a first inner lumen and a second inner lumen extending therethrough from a proximal guidewire port to a distal guidewire port which is adapted to receive a guidewire therein;

b) an expandable region having a proximal end and a distal end, said expandable region formed from said distal end of said catheter body in a one-piece configuration, said distal end of said expandable region having a passageway for the passage of said guidewire therethrough;

c) a flexible tubular guide element extending through said expandable region and having an interior in communication with said second inner lumen of said catheter body and adapted to receive said guidewire therein; and d) a control wire disposed within said first inner lumen of said catheter body having a distal end attached to said distal end of said expandable region and having means on said proximal end of said catheter body to move said control wire axially for adjusting the axial distance between said proximal and distal ends of said expandable region thereby adjusting the radial dimension of said expandable region; and e) said expandable region comprises a continuation of the catheter body having voids formed therein.

2. The intravascular catheter of claim 1 wherein said expandable region comprises a continuation of the catheter body having voids formed therein.

3. The intravascular catheter of claim 1 wherein, said expandable region has an interior lumen in fluid communication with said first inner lumen, said first inner lumen also in fluid communication with a port near said proximal end of said catheter body, said port providing for the introduction of a therapeutic fluid into said intravascular catheter for delivery to the artery.

4. The intravascular catheter of claim 1 wherein, said second inner lumen is defined at least in part by a sidewall section of said catheter body with said proximal guidewire port extending through said sidewall section.

5. The intravascular catheter of claim 4 wherein, said sidewall section has a longitudinally extending slit therein which facilitates the rapid removal of said catheter from said guidewire.

6. The intravascular catheter of claim 5 wherein, said longitudinally extending slit extends distally from said proximal guidewire port to a location proximally adjacent said distal end of said second inner lumen.

7. The intravascular catheter of claim 1 wherein, said proximal guidewire port of said second inner lumen is positioned about 20 cm to about 50 cm from said distal end of said expandable region.

8. The intravascular catheter of claim 1 wherein, a third inner lumen is provided in said catheter body which extends from said proximal end of said catheter body to a location proximal to said proximal guidewire port of said second inner lumen.

9. The intravascular catheter of claim 8 wherein, said third inner lumen has a stiffening element disposed therein.

10. The intravascular catheter of claim 1 wherein, said expandable region has a radiopaque material disposed therein.

11. The intravascular catheter of claim 1 wherein, said expandable region and said catheter body are made of stainless steel.

12. The intravascular catheter of claim 1 wherein, said expandable region and said catheter body are made of a nickel titanium alloy.

13. The intravascular catheter of claim 1 wherein, said expandable region and said catheter body are made of a polymer tubing.

14. A method for repairing an arterial vasculature having an occluded or partially occluded portion, comprising:

a) providing a catheter having
      i) a catheter body having a first inner lumen and a second inner lumen extending from a proximal guidewire port to a distal guidewire port which is adapted to receive a guidewire therein, said guidewire having a proximal end and a distal end;
      iii) an expandable region having a proximal end and a distal end, said expandable region formed from said distal end of said catheter body in a one-piece configuration, said distal end of said expandable region having a passageway for the passage of said guidewire therethrough, said expandable region comprising a continuation of the catheter body having voids therein;
      iv) a flexible tubular guide element extending through said expandable region and having an interior in communication with said second inner lumen of said catheter body and adapted to receive said guidewire therein; and
      v) a control wire disposed within said first inner lumen of said catheter body having a distal end attached to said distal end of said expandable region and having control means on a proximal end of said catheter body to move said control wire axially so as to adjust the axial distance between said proximal and distal ends of said expandable region and thereby adjust the radial dimension of said expandable region;

b) advancing said guidewire through said passageway provided in said expandable region, through said flexible tubular guiding element within said expandable region, through said second inner lumen of said catheter body, and out said proximal guidewire port;

c) positioning said distal end of said guidewire in the arterial vasculature across the site of the occlusion;

d) advancing said catheter body over said guidewire until said expandable region is positioned across the site of the occlusion; and e) manipulating said control means to move said control wire proximally thereby expanding said expandable region.

* * * * *

UNITED STATES PATENT AND TRADEMARK OFFICE
CERTIFICATE OF CORRECTION

PATENT NO. : 5,456,667
DATED : October 10, 1995
INVENTOR(S) : Kevin Ham, Michi E. Garrison, Farhad Khosravi It is certified that error appears in the above-indentified patent and that said Letters Patent is hereby corrected as shown below:

Claim 14, column 10, line 33, change "iii" to --ii--.

Claim 14, column 10, line 40, change "iv" to --iii--.

Claim 14, column 10, line 45, change "v" to --iv--.

Signed and Sealed this

Twenty-seventh Day of August, 1996

Attest:

BRUCE LEHMAN

*Attesting Officer*  *Commissioner of Patents and Trademarks*